US00PP25361P3

(12) United States Plant Patent
Jansen

(10) Patent No.: US PP25,361 P3
(45) Date of Patent: Mar. 17, 2015

(54) ***PENSTEMON* PLANT NAMED 'BOYSENBERRY TAFFY'**

(50) Latin Name: ***Penstemon* hybrid**
Varietal Denomination: Boysenberry Taffy

(71) Applicant: Terra Nova Nurseries, Inc., Canby, OR (US)

(72) Inventor: Robert D. Jansen, Naalehu, HI (US)

(73) Assignee: Terra Nova Nurseries, Inc., Canby, OR (US)

( * ) Notice: Subject to any disclaimer, the term of this patent is extended or adjusted under 35 U.S.C. 154(b) by 149 days.

(21) Appl. No.: 13/986,565

(22) Filed: May 14, 2013

(65) Prior Publication Data

US 2014/0345025 P1 Nov. 20, 2014

(51) Int. Cl.
*A01H 5/00* (2006.01)

(52) U.S. Cl.
USPC ..... Plt./465

(58) Field of Classification Search
CPC ..... A01H 5/02; A01H 5/00
USPC ..... Plt./465
See application file for complete search history.

*Primary Examiner* — June Hwu
(74) *Attorney, Agent, or Firm* — Klarquist Sparkman, LLP

(57) ABSTRACT

A new and distinct cultivar of *Penstemon* plant characterized by large dark red purple flowers, long bloom time, showy dark purple seed capsules when young, upright, well branched habit, with multiple crown from the base, clean-looking, deep green, attractive foliage, and excellent vigor.

1 Drawing Sheet

Botanical denomination: *Penstemon* hybrid.
Variety designation: 'Boysenberry Taffy'.

BACKGROUND OF THE INVENTION

The present invention relates to a new and distinct cultivar of *Penstemon*, given the name, 'Boysenberry Taffy'. *Penstemon* is in the family Scrophulariaceae. This plant originated a controlled breeding plan to create a compact, upright, large flowered series. The exact parents are unknown, unnamed proprietary plants. This cultivar was selected for its compact growing habit, large flowers in dense clusters, long flowering time, vigor, and clean attractive look. It is an ideal plant for a sunny border in full sun.

Compared to *Penstemon* 'Port Wine' (an unpatented plant), the new cultivar is shorter and has a lighter flower color.

Compared to *Penstemon* 'Raven' (an unpatented plant), the new cultivar has a smaller flowers and the habit isn't as well branched.

*Penstemon* 'Boysenberry Taffy' is uniquely distinguished by its:

1. large dark red purple flowers,
2. long bloom time,
3. showy dark purple seed capsules when young,
4. upright, well branched habit, with multiple crown from the base,
5. clean-looking, deep green, attractive foliage, and
6. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows the new cultivar in the trial field in full bloom in mid-July in Canby, Oreg.

DETAILED PLANT DESCRIPTION

The following is a detailed description of the new *Penstemon* cultivar based on observations of one year-old specimens grown outside in the ground in the trial beds in Canby, Oreg. in October. The color descriptions are all based on The Royal Horticultural Society Colour Chart, 5$^{th}$ edition.

Plant:

*Type.*—Herbaceous perennial.
*Form.*—Upright, branching.
*Cold hardiness.*—USDA Zone 7-10.
*Size.*—Grows to 60 cm wide and 60 cm high.
*Vigor.*—Excellent.
*Stem number.*—About 10 stems from the crown.
*Stem.*—Upright, grows to 49 cm long and 6 mm wide (at the base), glabrous at base to glandular pubescent toward peduncle, internodes grow to 4 cm long, Yellow Green 146B.
*Rooting.*—Roots easily from stem cuttings.

Leaf:

*Type.*—Simple.
*Arrangement.*—Opposite.
*Shape.*—Lanceolate.
*Venation.*—Pinnate, main vein on top and bottom side Yellow Green 145C.
*Margins.*—Entire.
*Apex.*—Acuminate.
*Base.*—Cuneate.
*Blade size.*—Grows to 10 cm long and 2.5 cm wide.

*Surface texture.*—Glabrous on both sides.

*Leaf color.*—Topside Green 137A, bottom side closest to Yellow Green 146A.

Inflorescence:

*Type.*—Terminal, many flowered, dense thyrse.

*Number of flowers per inflorescence.*—About 40.

*Size of inflorescence.*—Grows to 27 cm long and 11.5 cm wide.

*Peduncle.*—Grows to 5 cm long and 4 mm wide, pubescent, Yellow Green 146C.

*Pedicel.*—Grows to 7 mm long and 1 mm wide, pubescent, Yellow Green 146C in shade and Greyed Purple 183C in sun.

*Bloom period.*—Mid June to frost in October in Canby, Oreg. if spent flowers are removed.

Flower bud:

*Size.*—3 cm long and 13 mm wide.

*Description.*—Closed tubular, bulging, flattened ventrically.

*Color.*—Purple N79C.

Flower:

*Type.*—Zygomorphic, perfect.

*Shape.*—Tubular, bilabiate.

*Size.*—Grows to 4 cm long and 4 cm wide.

*Corolla description.*—Grows to 4 cm long and 4 cm wide; tube is funnel-form in the calyx for 5 mm long and 5 mm wide, inflating for 25 mm and flaring to 16 mm wide, 5 lobes, the two smaller top lobes flare back (each 13 mm wide and to 8 mm deep) and two larger lateral lobes flare out (15 mm wide and 11 mm deep), and the lower lobe flares down (16 mm wide and 12 mm deep), lobe margins entire to slightly jagged, tips obtuse; outside glandular pubescent, inside sparsely pubescent; outside color Purple N79B, inside color Purple N79B lightening to N79C in tube.

*Calyx description.*—9 mm deep and 11 mm wide, 5 overlapping lobes cut to the base, each lobe broadly ovate in shape, 9 mm deep and 8 mm wide, margins variable (entire, notched and frilled), tip acute, base cuneate, both sides Greyed Purple 187A in high light and Yellow Green 146C in low light, glabrous inside and glandular pubescent outside.

*Pistil description.*—1, 32 mm long, ovary 7 mm long and 3 mm wide, Yellow Green 145A; style 25 mm long and less than 1 mm wide, style Red Purple 61A on bottom half and White NN155C on top half, stigma White NN155C.

*Stamen description.*—5, one sterile without an anther, held within the corolla 14 mm long, filaments 25 to 30 mm long and White NN155C, anthers 3 mm wide and 3 mm deep, Greyed Purple N187A, pollen White NN155C.

*Fragrance.*—None.

*Lastingness.*—A flower lasts 5 to 6 days.

Fruit:

*Type.*—Capsule.

*Fertility.*—Good.

*Size.*—1.7 cm deep and 7 mm wide.

*Color.*—Purple N79B before they dry out to Brown 200A.

Seed:

*Shape.*—Irregular.

*Size.*—2 mm long.

*Color.*—Brown 200A.

Pests and diseases: The new cultivar is typical to the genus. No known resistances to pests or diseases. No problems have been found in Canby, Oreg.

I claim:

1. A new and distinct cultivar of *Penstemon* plant substantially as shown and described.

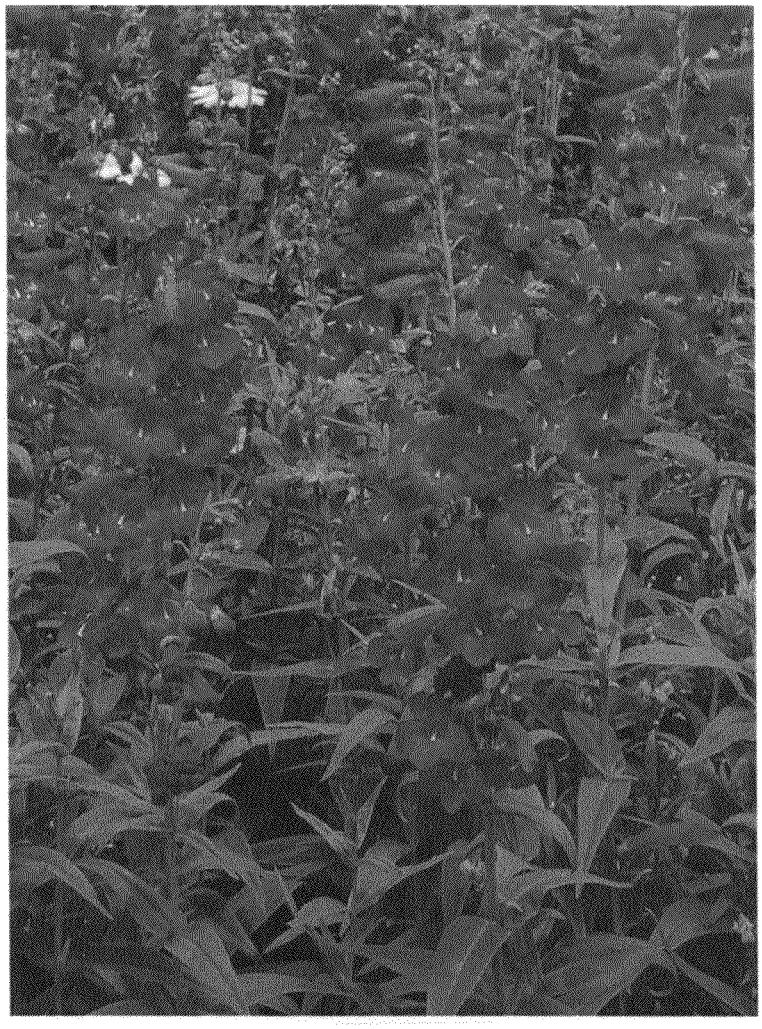

* * * * *